(12) United States Patent
Fogel

(10) Patent No.: US 11,654,083 B2
(45) Date of Patent: *May 23, 2023

(54) MEDICATION DELIVERY, DOSING AND SAFETY DEVICES, SYSTEMS AND KITS

(71) Applicant: ANAL-GESIC LLC, Lexington, MA (US)

(72) Inventor: Barry S. Fogel, Lexington, MA (US)

(73) Assignee: ANAL-GESIC LLC, Lexington, MA (US)

(*) Notice: Subject to any disclaimer, the term of this patent is extended or adjusted under 35 U.S.C. 154(b) by 73 days.

This patent is subject to a terminal disclaimer.

(21) Appl. No.: 17/328,650

(22) Filed: May 24, 2021

(65) Prior Publication Data

US 2021/0283013 A1    Sep. 16, 2021

Related U.S. Application Data

(63) Continuation of application No. 14/195,586, filed on Mar. 3, 2014, now Pat. No. 11,026,862, which is a
(Continued)

(51) Int. Cl.
*A61J 1/00* (2023.01)
*A61M 37/00* (2006.01)
(Continued)

(52) U.S. Cl.
CPC .............. *A61J 1/00* (2013.01); *A46B 5/04* (2013.01); *A46B 9/005* (2013.01); *A61B 42/00* (2016.02);
(Continued)

(58) Field of Classification Search
CPC ............. A61J 1/00; A61B 42/40; A61B 42/20
See application file for complete search history.

(56) References Cited

U.S. PATENT DOCUMENTS 2,637,031 A    5/1953  Friedman
3,326,450 A    6/1967  Langdon
(Continued)

FOREIGN PATENT DOCUMENTS

CN    2701788 Y    5/2005
CN    10104385 A    9/2007
(Continued)

OTHER PUBLICATIONS

CN Fourth Office Action on CN Patent Application No. 201380062027.7 dated Oct. 31, 2018 (19 pages).
(Continued)

*Primary Examiner* — Adam Marcetich
*Assistant Examiner* — Meagan Ngo
(74) *Attorney, Agent, or Firm* — Foley & Lardner LLP

(57) ABSTRACT

A product comprising a first compartment and a second compartment. The first compartment has first walls that define a reservoir. The first compartment includes a first lid enclosing a medicament within the reservoir. The second compartment has second walls that define a cavity. The second compartment includes a second lid enclosing a glove within the cavity. The first compartment and the second compartment are coupled together with the reservoir and the cavity separated and sealed from one another. The first walls of the first compartment and the second walls of the second compartment are semi-rigid or rigid.

19 Claims, 7 Drawing Sheets

Related U.S. Application Data continuation of application No. 13/786,905, filed on Mar. 6, 2013, now Pat. No. 8,663,177.

(60) Provisional application No. 61/707,765, filed on Sep. 28, 2012.

(51) Int. Cl.
| | | |
|---|---|---|
| *A46B 5/04* | (2006.01) | |
| *A46B 9/00* | (2006.01) | |
| *A61B 42/00* | (2016.01) | |
| *A61B 42/40* | (2016.01) | |
| *A61B 42/20* | (2016.01) | |
| *A61B 17/00* | (2006.01) | |

(52) U.S. Cl.
CPC .............. *A61B 42/20* (2016.02); *A61B 42/40* (2016.02); *A61M 37/00* (2013.01); *A61B 2017/00889* (2013.01); *A61B 2017/00893* (2013.01)

(56) References Cited

U.S. PATENT DOCUMENTS

| | | | |
|---|---|---|---|
| 4,051,950 A | 10/1977 | Jarund | |
| 4,689,935 A | 9/1987 | Harding | |
| 4,854,761 A | 8/1989 | Smith et al. | |
| 4,951,815 A * | 8/1990 | Ulbrich .................. | A61B 42/40 206/439 |
| 5,044,494 A | 9/1991 | Tamura | |
| 5,169,251 A | 12/1992 | Davis | |
| 5,348,153 A | 9/1994 | Cole | |
| 5,660,273 A | 8/1997 | Discko, Jr. | |
| 5,718,245 A | 2/1998 | Horn | |
| 5,740,943 A | 4/1998 | Shields et al. | |
| 5,761,743 A | 6/1998 | Andrews et al. | |
| 5,934,462 A * | 8/1999 | Gregory .................. | A61B 42/40 206/278 |
| 5,947,275 A | 9/1999 | Hess | |
| 6,012,586 A | 1/2000 | Misra | |
| 6,123,676 A | 9/2000 | Anapliotis | |
| 6,321,750 B1 | 11/2001 | Kelly | |
| 7,056,309 B1 | 6/2006 | Hennigan | |
| D533,314 S | 12/2006 | Schiazza | |
| 8,663,177 B1 | 3/2014 | Fogel | |
| 2002/0016517 A1 | 2/2002 | Kaspi et al. | |
| 2002/0148855 A1 | 10/2002 | Sokolsky et al. | |
| 2002/0152538 A1 | 10/2002 | McDevitt et al. | |
| 2003/0120180 A1 | 6/2003 | Kaylor et al. | |
| 2004/0016064 A1 | 1/2004 | Vena | |
| 2004/0019336 A1 | 1/2004 | Temple et al. | |
| 2006/0137070 A1 | 6/2006 | Yang et al. | |
| 2007/0012714 A1* | 1/2007 | Bagwell .................. | A47K 5/12 221/33 |
| 2007/0025932 A1 | 2/2007 | Ponce et al. | |
| 2007/0205127 A1 | 9/2007 | Barndt et al. | |
| 2007/0218132 A1 | 9/2007 | De Simone | |
| 2007/0281906 A1 | 12/2007 | Dalton et al. | |
| 2008/0034460 A1 | 2/2008 | Keene | |
| 2008/0109928 A1 | 5/2008 | Bae | |
| 2008/0289634 A1* | 11/2008 | Kassman .................. | A61F 6/00 604/310 |
| 2009/0014351 A1 | 1/2009 | Walker | |
| 2009/0047228 A1 | 2/2009 | Guerchet | |
| 2009/0048579 A1 | 2/2009 | Glassman et al. | |
| 2010/0065576 A1 | 3/2010 | Verheij | |
| 2011/0036746 A1* | 2/2011 | Bear .................. | G09B 19/0084 206/572 |
| 2011/0062051 A1 | 3/2011 | Miller | |
| 2011/0062179 A1 | 3/2011 | Stollery et al. | |
| 2011/0124736 A1 | 5/2011 | Trogden et al. | |
| 2011/0297170 A1 | 12/2011 | Pitts et al. | |
| 2013/0012892 A1 | 1/2013 | Brown | |
| 2013/0117901 A1 | 5/2013 | Schrecongost | |
| 2017/0333410 A1 | 11/2017 | Babul | |
| 2020/0152538 A1 | 5/2020 | Myung et al. | |

FOREIGN PATENT DOCUMENTS

| | | |
|---|---|---|
| CN | 101043856 A | 9/2007 |
| EP | 0 803 231 A | 10/1997 |
| EP | 1 731 113 | 8/2013 |
| EP | 2 255 835 | 8/2014 |
| FR | 1333881 A | 8/1963 |
| GB | 2 108 921 A | 5/1983 |
| JP | 2005-513513 | 5/2005 |
| JP | 2007-089599 | 4/2007 |
| JP | 2011-024939 | 2/2011 |
| WO | WO-03/056954 | 7/2003 |
| WO | WO-2004/035072 | 4/2004 |
| WO | WO-2006/080035 A1 | 8/2006 |
| WO | WO-2009/119512 | 10/2009 |
| WO | WO-2008/044282 | 12/2009 |
| WO | WO-2014/052680 A1 | 4/2014 |

OTHER PUBLICATIONS

CN Office Action for Application No. 201380062027.7 dated Aug. 25, 2017. (7 pages).

CN Office Action for Application No. 201380062027.7 dated Feb. 24, 2018. (26 pages).

CN Office Action on CN Patent Application No. 201380062027.7 dated May 17, 2019 (20 pages).

Dobrydneva et al. "Dietary Phytoestrogens and Their Synthetic Structural Analogues as Calcium Channel Blockers in Human Platelets". Journal of Cardiovascular Pharmacology. 40: 399-410. Philadelphia, 2002.

Foreign Action other than Search Report on CA 2925665 dated Apr. 22, 2020.

Foreign Action other than Search Report on CA 2925665 dated Jun. 20, 2019.

Non-Final Office Action for U.S. Appl. No. 13/786,905 dated Jul. 31, 2013, 11 pages.

* cited by examiner

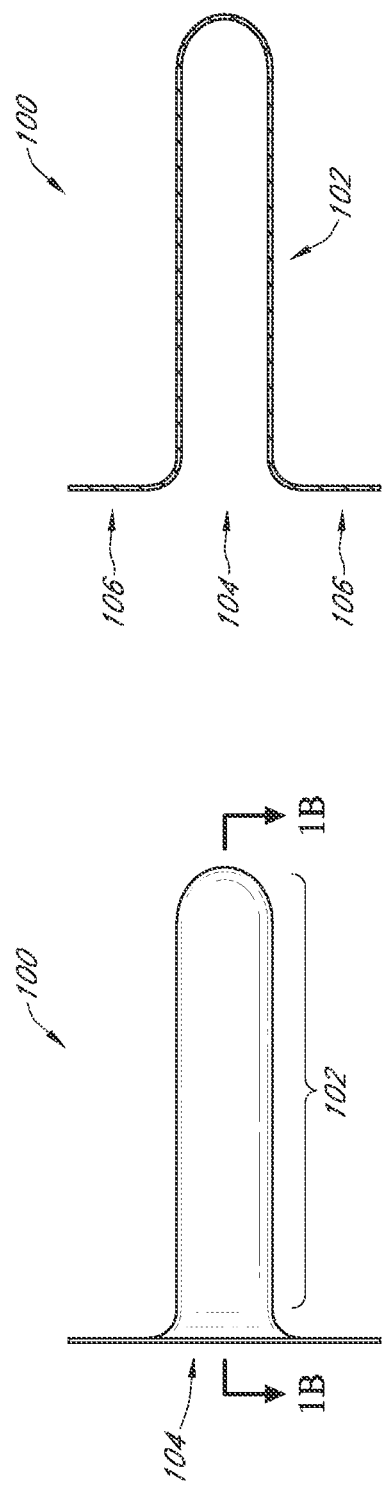
FIG. 1A
FIG. 1B
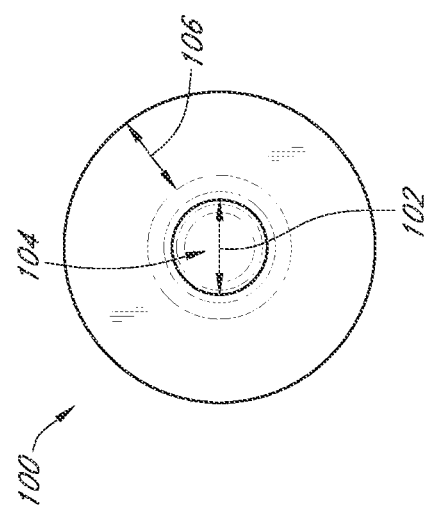
FIG. 2

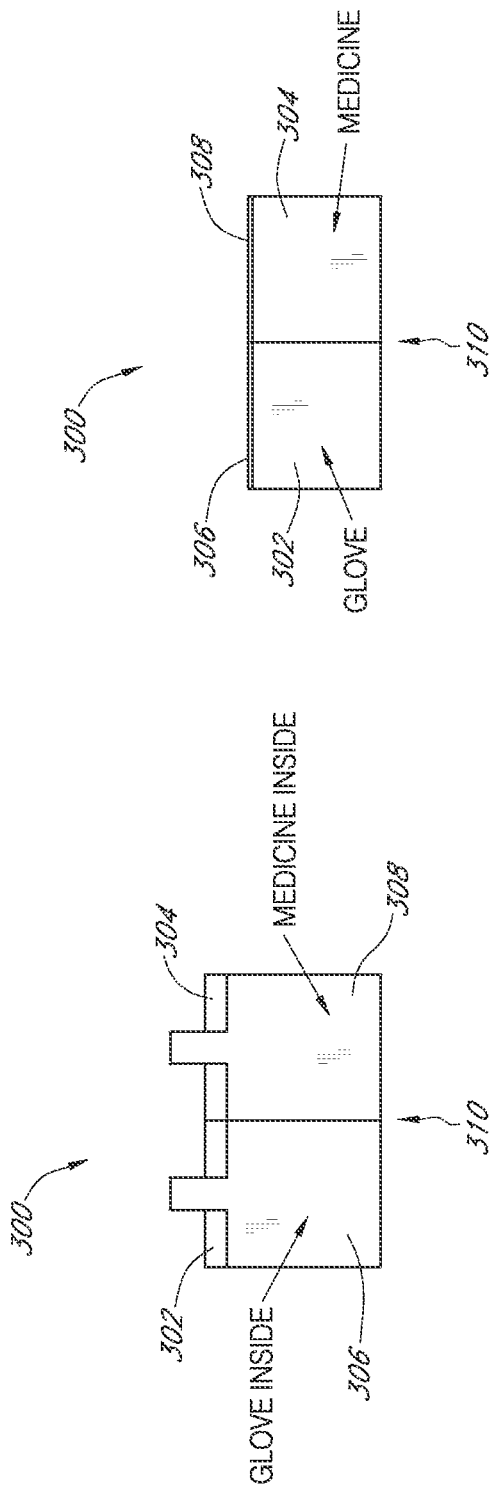

US 11,654,083 B2

MEDICATION DELIVERY, DOSING AND SAFETY DEVICES, SYSTEMS AND KITS

CROSS-REFERENCE TO RELATED PATENT APPLICATIONS

This application is a continuation of U.S. patent application Ser. No. 14/195,586, filed Mar. 3, 2014, which is a continuation of U.S. patent application Ser. No. 13/786,905, filed Mar. 6, 2013, which claims the benefit of and priority to U.S. Provisional Patent Application No. 61/707,765, filed Sep. 28, 2012, all of which are incorporated herein by reference in their entireties.

FIELD

Embodiments generally relate to devices, systems, kits and methods of delivering or administering a medicament to a recipient in a safe, sanitary, consistent and/or efficacious manner.

BACKGROUND

A number of medications, health products, beauty products, etc. are applied topically to the body of a recipient—either the skin or to some externally accessible organ such as the eye, the mouth, the vagina, the anus, etc. A variety of specialized applicator devices and methods of application are available and utilized for topical application to various parts of the body. Beyond devices, many such products are applied by the hand of the recipient or by the hand of a third party (e.g., healthcare professional) to the recipient.

Described herein are improved devices, kits, systems and methods for packaging and delivery of such products.

SUMMARY

Embodiments described herein generally relate to improved devices, systems, kits, products and methods related to medicament application. Many medications are applied topically by a user. In some cases the topical application may be to "private parts" such as the anal or vaginal region of the body; users may find the application of medication to such regions unpleasant, inconvenient or undesirable with the consequence that their usage of the medication is inconsistent or non-compliant with the prescriber's recommendation. In other cases topical application with a non-sterile finger or applicator may lead to infection of the area to which the medication is applied. Other challenges with the topical application of such medications include improper dosing due to too little or too much medication being applied—for example, because of the lack of precision of dipping the finger into a container or in removing medication from a tube. In some cases the lack of appropriate dosing can be dangerous for the recipient, as in situations where the topical medication is systemically absorbed and has systemic toxicity at blood levels beyond a certain threshold. Also, the repeated contacting of the medication with a non-sterile finger or applicator can result in contamination of the medication. Furthermore, medication containers may be of a size inconvenient for portability or non-compliant with airline security restrictions.

In other cases, the medication can be harmful or unpleasant if contacted with the hands or finger of the user while it is being applied, such that medical gloves or another blocking device are necessary. Unfortunately, the use of gloves, such as latex gloves, can be inconvenient, requiring bringing gloves to work or on travel, and wasteful because an entire new glove must be used and disposed of with each application of the medication. (The use of plastic wrap or other makeshift barriers to cover the finger is inconvenient and does not ensure sterility or cleanliness of disposal after use.

These and various other facts can result in less compliance with product usage regimes and guidelines. Described herein are devices, systems, kits and methods that address one or more of the various (non-limiting list of) problems that have been identified and discussed.

Anal diseases such as anal fissure offer an example of a condition where there is a need for such devices, kits, systems and methods. Anal diseases are widely prevalent in the general population. In addition to anal fissure, such conditions include hemorrhoids and idiopathic pruritus ani, as well as a range of infectious, inflammatory, and neoplastic conditions. Many of these conditions have topical treatments, typically creams or ointments applied one or more times daily. Suppositories are useful for some of these conditions, but not for all of them, since suppositories do not address the need in some conditions to deliver medication to the perianal skin, and their delivery of medication to the anal mucosa cannot be focused. Moreover a suppository can migrate proximally into the rectum before it has delivered the full dose of drug to the anal area where it is needed.

Creams or ointments for anal diseases typically are supplied in tubes, jars, or other multiple-dose containers, or they can be packaged for single doses, typically in foil wrappers. Multiple dose containers are more common. The medication is typically applied using one finger of a hand in a disposable glove; alternatively the patient wraps the finger in plastic wrap, uses a cotton ball, or simply uses an unprotected finger and washes the hands afterwards. If the finger is not gloved the application may be unsanitary and unpleasant for the patient, and when the finger is dipped into the container bacterial contamination can be introduced. If water is not readily available it may not be feasible to wash the hands immediately after applying the medication. However, patients don't always have ready access throughout the day to disposable gloves, and carrying them in addition to the medication adds expense and inconvenience. Whether the dose is given with or without a glove, the amount of medication given typically is imprecise: The patient either dips a finger into a jar of the cream or ointment, squeezes a line of medication of a certain length onto a finger, or aims to form a glob of medication "the size of a grain of rice" or "the size of a pea" (actual descriptions from published studies of topical anal fissure treatments.) Precise measurement in any case is inconvenient and usually not done. The lack of precise dosing is a particular concern when the topical anal medication is systemically absorbed. An excessively large topical dose can in that situation produce significant systemic adverse effects. On the other hand, an insufficient dose can be ineffective. In the case of anal fissures, three topical treatments—nitroglycerin, diltiazem (and other calcium channel blockers), and doxazosin (and other alpha adrenergic blocking drugs)—all can lower blood pressure if a sufficient amount is systemically absorbed, and nitroglycerin can have a potentially fatal interaction with drugs (PDE5 inhibitors) used to treat erectile dysfunction in men, with a risk that is greater when a higher dose of nitroglycerin is administered.

Thus, there is a need for a simple, convenient, sanitary way to deliver a precise dose of a topical anal cream or ointment. A method or device for doing this would improve compliance with topical treatment for anal conditions, particularly when the treatment involved required application several times a day. It would also reduce adverse effects of treatment due to systemic absorption of a topical drug, and lack of efficacy due to inadequate or inconsistent dosing. One potential consequence of these improvements may be that a topical drug available by prescription only becomes sufficiently safe and easy to apply that it is approvable for sale over the counter without a prescription. This consequence would give more people with these conditions timely access effective treatment.

Embodiments herein provide methods, products, kits, devices and systems that can be applied to many topical agents and medications, including those applied to other regions of the body such as, for example, the vaginal region, or to the conjunctiva of the eye.

Some embodiments relate to kits that include for example, a reservoir that includes a medicament, and the kits also can include a medicament application device that provides a protection between the medicament when it is being handled or applied and at least some of the skin on the hand of the user of the medicament application device, the medicament being in a form suitable for topical application using the application device, and the application device being securable to at least a portion of the hand of the user and covering at least a portion of the hand of the user. The reservoir can include, for example, a single application dosage of the medicament, only an amount of medication that does not exceed an amount that can be safely given, and/or an amount of medicament that is efficacious for a patient.

The medicament can include, for example, one or more of a cream, a gel, a foam, an ointment, a lotion, a balm, a salve, a liquid, a powder, a slurry, a suspension, a patch, an adhesive, a tape, a paste, a sponge, a tincture, and the like. In some aspects, the medicament can be medicated while in others it can be non-medicated. In some embodiments, the medicament can include, for example, an agent such as a hormone, an antibiotic, an anesthetic, an antiseptic, an anti-microbial (e.g., anti-fungal and anti-microbial), an anti-impotence medication, an anti-inflammatory, antihistamine, anti-allergy, an anti-pain medication, an analgesic, an acne medication, an anti-wrinkle or anti-aging compound, a hair dye, a moisturizer, a growth hair or skin growth promoter, a cleanser, or any other like material. The medicament can be, for example, a medicament for treating a medical condition of the anal region or vaginal region of a patient. The medical condition of the anal region can be, for example, pruritus ani, anal pain, an anal fissure, an anal itch, a hemorrhoid, anal neoplasm, anal inflammation, a sexually transmitted disease, an infection, or the like. The medical condition of the vaginal region can be, for example, one or more of an infection, a vaginal itch, vaginitis, a vaginal sexually transmitted disease, a vaginal cancer, and the like.

In some embodiments, the medicament application device can be, for example, a single-finger glove that covers at least the distal portion of one finger on the hand of the user. In still other embodiments, the medication application device can be, for example, a two-finger glove that covers one or two digits of the hand of the user (e.g., a single lumen or cavity glove that fits two fingers together, or a dual lumen glove that has a single lumen or cavity that fits each of two separate fingers). For example, the single or two finger gloves respectively can be a device that a glove covers at least the distal portion of a single digit of the hand of the user, a glove that covers at least the distal portion of two fingers (e.g., the index finger and middle finger), etc. In some embodiments, the glove can be configured to substantially cover at least the distal and middle phalanges, at least the distal, middle and proximal phalanges, or the entire digit including and distal to the metacarpophalangeal joint of a finger or two adjacent fingers (e.g., index and middle fingers)=, for example. The glove can include, for example, a first distal portion that substantially contacts the digit (or majority of the two digits) or contacts at least a majority of the digit (or majority of the two digits), and a second proximal portion comprising a skirt portion having a peripheral diameter at its widest point that wider than the diameter of the first distal portion. The skirt can extend radially from the first distal portion to a peripheral edge, for example. The skirt may cover, for example, at least a portion of the hand at the base of the digit (or the base of the two digits), for example, at least a portion of the hand proximal to the metacarpophalangeal joint (or joints). Typically a single finger glove would cover all or part of the index, middle, or fifth finger; a two-finger glove would cover all or part of the index and middle finger simultaneously. It should be understood that in some embodiments the devices can specifically exclude gloves or other devices that cover all five fingers or that cover the entire hand. For example, some embodiments specifically exclude gloves or devices that fit or cover three or more fingers, or cover two non-adjacent fingers.

In some embodiments, the medicament application device can be, for example, a glove that covers at least the distal portion of more than two digits of the hand of the user, for example, all of the digits of the hand. In some aspects, the medication application device can be a typical five-fingered glove. In some embodiments, such gloves are packaged individually in a manner such that the gloves can fit into the pocket or wallet of the user, preferably unobtrusively. The packaging can be of size such that the packaged glove can be included in a kit with a medicament as described elsewhere herein. Any suitable packaging can be used, including the various configuration described herein.

In some aspects, the packaging can be a foil, plastic, paper, or other like material that forms an envelope or pouch package, which can have for example, a think profile when the glove is within the package. For example, without being limited thereto, the package can be square or rectangular with an inner cavity or lumen. Without being limited thereto, the package can have dimensions of approximately 10 mm to 60 mm in width, 30 mm to 100 mm in length between 2 mm and 10 mm in thickness at the thickest point when a glove is in the package. In some aspects the gloves can be packaged so that upon opening the package, a portion of the skirt or proximal opening is presented to the user and available for grasping in order to remove the glove from the package without contacting other portions of the glove. In some aspects the glove can be packaged using vacuum or shrink wrap technology in order to minimize the size of the package.

In some embodiments, the medicament application device may include, for example, one or more of latex, vinyl (polyvinyl chloride), rubber, butyl rubber, nitrile rubber, Viton, Neoprene, polyisoprene, plastic, paper, cotton, vinyl polyvinyl alcohol, and the like. The medicament application device can be, for example, elastic or flexible. The medicament application device can be, for example, suitable for a single use or be disposable. It can be made of a material that is biodegradable and or that can septic safe or flushable down a toilet (e.g., per regulations, laws and/or ordinances).

In still some embodiments, the kits may include, for example, at least two compartments, one comprising the reservoir and the other comprising or configured to contain the medicament application device. In some aspects, the at least two compartments may at least partially share at least one wall. The at least partially shared wall may include, for example, one or more of the dividing edge of dual compartment foil or plastic pouch, the shared wall of each of the two separate compartments, a removable or openable lid of the reservoir and a wall of the compartment comprising the medicament application device, a removable or openable lid of the reservoir compartment and a wall of the compartment comprising the medicament application device, a removable or openable lid of the compartment comprising the medicament application device and a wall of the reservoir compartment, and a lid of either or both of reservoir compartment and the compartment comprising the medicament application device. The kit may include, for example, a compartment comprising an at least partially rigid material, at least two compartments comprising an at least partially rigid material, one or two compartments at least partially comprising a non-rigid material, or at least one compartment at least partially comprising a rigid material and at least on compartment at least partially comprising a non-rigid material. The kit may include, for example, at least a two compartment container with a lid and sides, the sides comprising a rigid material and the lid configured to be removed. The rigid material may include, for example, a plastic, a polymer, a metal, a foil, a paper, or the like. The non-rigid material may include, for example, a plastic, a polymer, a rubber, a metal, a foil, a paper, or the like. The kit may include, for example, a container that includes a foil, the container including or having at least two separate compartments at least partially connected on one side, wherein each compartment is configured to be separately opened. The kit may include, for example, at least one compartment that comprises a rigid material and a separate compartment comprising a non-rigid material.

In some embodiments the medicament application device can be included in a separate container from the medicament reservoir. The reservoir may be configured to permit a digit of the user to remove a dosage of the medicament by dipping and/or scraping, and/or may be configured to expel the medicament onto one or more covered digits upon the application of force to the reservoir.

Also, some embodiments relate to methods of applying a medicament, which may include, for example, providing a kit as described above and elsewhere herein; putting the medicament application device onto the appropriate portion of the hand of the user; removing an amount of the medicament from the reservoir, and contacting at least some of the medicament to a region of the body of a patient that is to be treated. The methods further may include, for example, removing the medicament application device from the hand of the user. The removing of the device may include, for example, grasping at least a portion of the proximal edge of the device and pulling the device in a direction that is distal to the user such that after removal the inside wall of the device is on the external side of the device. The methods further may include, for example, discarding the removed medicament application device. The methods further may include, for example, discarding the medicament reservoir.

Some embodiments relate to products that include a plurality of the kits as described above and elsewhere herein. The plurality of kits may include, for example, a supply of medicament for a desired period of treatment, for example, a period of 1 day, 2, days, 3 days, 4 days, 5 days, 6 days, 7 days, 8, days, 9 days, 10 days, 2 weeks, 3 weeks, 1 month, 90 days, 120 days, or any other period of time or sub-range within the listed time periods. The product may include, for example, a separate kit for each administration of the medicament. The medicament for the products can be, for example, one that is administered once daily or multiple times per day.

Further, some embodiments relate to packages that include at least two compartments, one compartment that includes a one-finger glove and another compartment that includes a measured amount of a medication for a single administration. The one-finger glove may include, for example, a distal portion that contacts substantially all of the perimeter area of the finger and a proximal skirt portion having a greater diameter than the distal portion that fans out and covers a part of the hand that is adjacent to the finger within the distal portion. The medication of the packages can be, for example, for treating an anal condition such as an anal fissure. The medication may include, for example, one or more of nitroglycerin, diltiazem, doxazosin, other calcium channel blockers, other alpha adrenergic blocking drugs, and the like.

Some embodiments relate to one-finger gloves that include a distal portion that contacts substantially all (e.g., greater than 50%, about 60%, about 70%, about 80%, about 90%, about 95%, about 96%, about 97%, about 98%, about 99%, or any value or sub-range there between) of the perimeter area of an inserted finger and a proximal skirt portion having a greater diameter (e.g., inner or outer diameter) than the distal portion, the proximal skirt portion configured to fan out and cover a part of the hand that is adjacent to the finger within the distal portion.

The systems, devices, and methods disclosed herein each have several aspects, no single one of which is solely responsible for their desirable attributes. Without limiting the scope of the claims, some prominent features will now be discussed briefly. Numerous other embodiments are also contemplated, including embodiments that have fewer, additional, and/or different components, steps, features, objects, benefits, and advantages. The components, aspects, and steps may also be arranged and ordered differently. After considering this discussion, and particularly after reading the section entitled "Detailed Description of Certain Embodiments," one will understand how the features of the devices and methods disclosed herein can provide advantages over other known devices and methods.

BRIEF DESCRIPTION OF THE DRAWINGS

The above-mentioned features, as well as other features, aspects, and advantages of the present technology will now be described in connection with various embodiments of the invention, in reference to the accompanying drawings. The illustrated embodiments, however, are merely examples and are not intended to limit the invention.

FIG. 1A depicts a side view of a non-limiting example of one embodiment of an application device according to some embodiments.

FIG. 1B depicts a cross-sectional side view of one embodiment of the application device of FIG. 1A.

FIG. 2 depicts a bottom view of the application device of FIGS. 1A-1B.

FIG. 4 depicts a top view of a non-limiting example of one embodiment of dual compartment container device or system that can be used in the kits and products described herein, that includes an application device (e.g., a glove or "single-finger" glove) and a medication compartment that can include a specific amount or dosage of the medicine.

FIG. 5 depicts side view of the device or system of FIG. 4 that includes an application device (e.g., a glove or "single-finger" glove) and a medication compartment that can include a specific amount or dosage of the medicine.

DETAILED DESCRIPTION

Figure 3A:
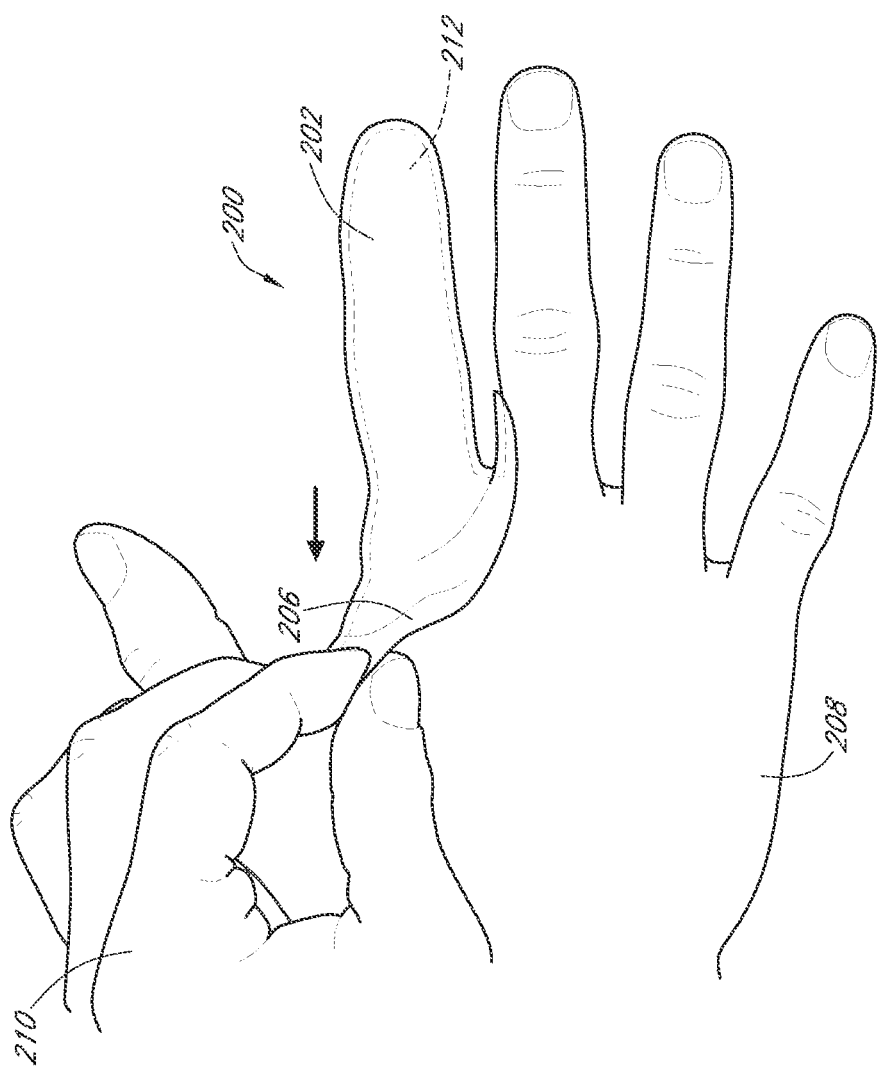
FIG. 3A depicts a non-limiting example of a user putting on an application device according to some embodiments, including for example, a device according to FIGS. 1A, 1B and 1C.

In the following detailed description, reference is made to the accompanying drawings, which form a part of the present disclosure. In the drawings, similar symbols typically identify similar components, unless context dictates otherwise. The illustrative embodiments described in the detailed description, drawings, and claims are not meant to be limiting. Other embodiments may be utilized, and other changes may be made, without departing from the spirit or scope of the subject matter presented here. It will be readily understood that the aspects of the present disclosure, as generally described herein, and illustrated in the Figures, can be arranged, substituted, combined, and designed in a wide variety of different configurations, all of which are explicitly contemplated and form part of this disclosure.

As discussed above, there are a number of problems, challenges, or inconveniences associated with the administration of certain topical medications (and other topically applied products). Generally, embodiments disclosed herein relate to devices, systems, kits, products and methods for more effectively, conveniently, consistently and/or safely administering such medications and products.

In some embodiments topical medications or other types of products may be administered, packaged, or included in kits or systems that take into account the challenges or constraints detailed herein, including one or more of the following:

1) In some non-limiting aspects the medication must be kept sterile or at least very clean until it is applied, which can require careful hand washing before applying the medication, for example;
2) In some non-limiting aspects the dose of the topical medication must be limited because of a concern about side effects from systemic absorption or other side effects from too much or even too little medication;
3) In some non-limiting aspects the medication can irritate the skin of the finger, can be absorbed through the finger and cause systemic or local adverse effects, or cause adverse effects if the finger touches the mouth or eyes while some medication remains on it; thus this can require careful hand washing afterwards;
4) In some non-limiting aspects, touching the area to which the medication is applied may soil an ungloved finger or cause an ungloved finger to have an unpleasant smell; which again can require careful hand washing afterwards, which may not always be convenient or possible, for example, if water is not readily available at the time the medication is needed or is scheduled to be applied.

Embodiments herein generally relate to kits, products, devices, systems and methods that address one or more of the concerns discussed herein, and/or which provide one or more benefits to the patient, the person administering the medication (if different from the patient), and to society to environmental and financial savings derived from the subject matter.

Some embodiments relate to kits that include, for example, a reservoir that includes a medicament. Those reservoirs or compartments comprising the reservoirs can be as described elsewhere herein. Additionally the kits can include a medicament application device that provides a barrier or a protection between the medicament when it is being handled or applied and at least some of the skin on the hand of the user of the medicament application device. The medicament application device also can shield or provide a protection against contamination of the hand of the user when the device contacts regions of the body such as the anal or vaginal region, mucous membranes, etc. Furthermore, the application device can provide protection or act as a barrier preventing body fluids and materials from contacting the hand of the user. Generally, in some embodiments, the medicament of the reservoir can be in a form suitable for topical application when using the application device.

In some aspects, the reservoir may include, for example, an amount of medicament sufficient for a single dose application. For example, the amount of medication can be metered or measured to ensure that it is the proper amount for a single application. The reservoir can consist of, consist essentially of (e.g., medicament and other materials that do not materially affect the basic and novel characteristics of the claimed reservoirs, kits, packages, products and/or methods), contain or include only an amount of medication that does not exceed an amount that can be safely given or a dosage that is efficacious for a patient, for example. As noted above, some medications can be dangerous if too much is give and not efficacious if too little is given. Having a reservoir with a measured or metered amount can facilitate the patient getting a safe and effective dose each time. In some embodiments the amount of medicament that is contained can be approximately 50 mg to 10 grams or any sub amount or sub range there between. Without being limited thereto, a single dose of a topical medication for anal pain would rarely be more than a gram, but for other topical indications up to 10 times that amount might be used.

The reservoir can be configured to permit a digit (e.g., the index figure) of the user remove the desired dosage of the medicament by dipping, scooping and/or scraping. In some embodiments the reservoir can be configured to expel the medicament onto one or more covered digits upon the application of force to the reservoir. For example, the reservoir can be squeezed to expel the medicament from the containment reservoir, which might be a pouch, for example.

An additional potential benefit of the single dosage reservoirs is that they can be more convenient for transport to work or other daily destinations or for transport during travel. Multi-dose containers, such as jars or tubes may be inconvenient to transport due to size constraints for example. In the case of travel such containers may exceed allowable size or volume limits, for example, for airport security. Furthermore, the single dose reservoirs or containers can prevent or avoid contamination problems that can occur with larger containers that repeatedly are exposed to potential contaminants in the air and environment, and on the fingers or hands of the user that are repeatedly dipped into or contacted with such containers. The single dosage reservoirs (and the glove compartments or packaging) can also facilitate disposal of the reservoir, the glove and/or the packaging around the glove and reservoir. For example, the packaging for a single reservoir/glove kit can be small enough to fit into any trash receptacle or even in a purse, pocket or small bag. In some embodiments, the packaging can be configured or made from a material that permits it to be flushed down a toilet or other liquid disposal device. In some aspects the packaging, wrapper and/or glove can be biodegradable.

It should be noted that single dose or single use reservoirs or containers have been discussed. It should be noted that single day reservoirs or containers that include sufficient doses for multiple applications within a day, also are contemplated. In such embodiments, the kits can include multiple application devices for use during a given day (e.g., one application device for each application). It should be understood that multi-dose containers also are contemplated. In some embodiments even multi-dose (e.g., 2-5 doses) containers can be better than a container with larger amounts of medicament. In such embodiments, the kits can include a greater number of medicament application devices (e.g., preferably one for each use), which are described in more detail below. However, in some preferred embodiments, the kits can include a multitude of containers where each container only includes a single application amount or single dosage of the medication. Such containers can be disposed of after a single application without having to waste any significant amount of medication.

Any suitable medicament can be used with the kits, devices, systems and products described herein. While medicaments the include medicinal materials are contemplated, other materials that can provide health, wellness and/or beauty benefits also are contemplated regardless of whether such materials include what is technically a medicinal product. Thus, non-medicinal agents that are to be topically applied also can be used with the instant technology. The medicament can have or include one more of a cream, a gel, a foam, an ointment, a lotion, a balm, a salve, a liquid, a suppository, a depot formulation, a powder, a slurry, a suspension, a patch, an adhesive, a tape, a paste, a sponge, and a tincture. Examples of agents that can be included a hormone, an antibiotic, an anesthetic, an antiseptic, an anti-microbial (e.g., anti-fungal and anti-microbial), an anti-impotence medication, an anti-inflammatory, antihistamine, anti-allergy, an anti-pain medication, an analgesic, an acne medication, an anti-wrinkle or anti-aging compound, a hair dye, a moisturizer, a growth hair or skin growth promoter, a cleanser, or any other like agent or otherwise suitable agent.

In some embodiments the medicament can be an agent useful for treating a medical condition of the anal region or vaginal region of a patient, for example. Non-limiting examples of medical conditions of the anal region include pruritus ani, anal pain, an anal fissure, an anal itch, a hemorrhoid, anal neoplasm, anal inflammation, a sexually transmitted disease and an infection (e.g., bacterial, fungal, viral, etc.). Non-limiting examples of specific medication that can be used for anal conditions, such as fissures, are nitroglycerin, diltiazem (and other calcium channel blockers), and doxazosin (and other alpha adrenergic blocking drugs). Several non-limiting examples of vaginal medical conditions are an infection (e.g., bacterial, fungal, yeast, viral, etc.), a vaginal itch, vaginitis, a vaginal sexually transmitted disease, and a vaginal cancer or neoplasm.

As noted above, topical medications present a number of challenges or inconveniences insofar as many are applied by the patient's fingers. That can be unpleasant, for example, when the applying medicaments to the anus or anal region due to the discomfort, the odor, the pain, etc. Certain medications also are inconvenient due to causing irritation to the fingers, leaving noxious residue on the fingers that can harmful if contacted with the eyes, mouth or nose, and/or can leave an unpleasant odor or discoloring on the fingers. The use of latex and other gloves potentially can alleviate some these problems, but can lead to their own problems. First, the gloves themselves may provide more protection than is absolutely necessary since the medicament may only need to contact a single finger. Also, for a single use, it can be preferred to minimize the amount of waste that is generated by not having to throw away a whole glove with all of the excess material if that is not needed. Additionally, many patients have sensitivity or allergies to latex and other types of materials commonly used in gloves such that minimizing the amount of material that contacts the skin of the user can be beneficial. It should be understood that such gloves are contemplated for use in some embodiments as medicament application devices, however, some of the embodiments and application devices described herein can provide a more environmentally friendly and convenient alternative.

The medicament application devices can be configured so as to be securable to at least a portion of the hand of the user and/or so that it can cover at least a portion of the hand of the user. In some embodiments, the medicament application devices can be "gloves" that cover less than the entire hand or less than all of the fingers and/or thumb (i.e., "digits") of the hand. For example, the devices or "gloves" can cover at least the distal portion of one or two digits of the hand of the user. In some aspects the gloves can cover at least the distal portion of one or two of the adjacent digits (e.g., index and middle fingers) of the hand of the user, for example. In some aspects the gloves can be a single or one finger "glove" that can cover at least the distal portion of a single digit of the hand of the user. The devices and various "gloves" described herein can cover at least the distal and middle phalanges of one or two adjacent fingers, at least the distal, middle and proximal phalanxes of one or two adjacent fingers, or the entire digit distal to the metacarpophalangeal junction of one or two adjacent fingers, for example. The devices can be configured to fit or accommodate a single digit within the glove, including by contacting substantially the entire digit or to accommodate two fingers into a single cavity of the glove. The devices can be configured to fit or accommodate two digits within the glove, including by contacting substantially the entirety of the digits. For example, the devices can be configured or sized to be tight around a digit of the hand or tightly/securely around two digits of the hand. The devices can have an internal diameter that substantially matches or matches the diameter of the digit or two digits at a given point. The devices can be flexible or made of a flexible material (e.g., latex or neoprene), or the devices can be made of a material that does not stretch.

In some aspects the gloves can terminate or have at their proximal end a roll of material that can provide strength or adding securement for the device. In other embodiments, the gloves or devices can specifically exclude devices that have the roll or thicker portion at the end, for example, which aids in securing the device onto the finger. For example, the devices can exclude, in some embodiments, the roll or thickened rubber as is found at the proximal end of a condom. It should be understand that the "gloves" and devices can "at least partially" cover the digits and/or hand, which denotes coverage of less than all of the digit or hand, but the gloves also can cover all the finger, finger and thumb or digits. The gloves and devices can cover substantially all of a given digit, hand or region of a digit or hand where "substantially" can mean from between about 51% to about 99.9% of the given region or any value or sub-range there between (e.g., 60%, 70%, 75%, 80%, 85%, 90%, 91%, 92%, 93%, 94%, 95%, 96%, 97%, 98% or 99%, or any sub-range or sub-value there between).

In some embodiments, the kits described herein can include a five-fingered glove, for example, that is individual packaged. In some embodiments, such gloves are packaged individually in a manner such that the gloves can fit into the pocket or wallet of the user, preferably unobtrusively. The packaging can be of size such that the packaged glove can be included in a kit with a medicament as described elsewhere herein. Any suitable packaging can be used, including the various configuration described herein. In some aspects, the packaging can be a foil, plastic, paper, or other like material that forms an envelope or pouch package, which can have for example, a think profile when the glove is within the package. For example, without being limited thereto, the package can be square or rectangular with an inner cavity or lumen. Without being limited thereto, the package can have dimensions of approximately 10 mm to 60 mm in width, 30 mm to 100 mm in length between 2 mm and 10 mm in thickness at the thickets point when a glove is in the package. In some aspects the gloves can be packaged so that upon opening the package, a portion of the skirt or proximal opening is presented to the user and available for grasping in order to remove the glove from the package without contacting other portions of the glove. In some aspects the glove can be packaged using vacuum or shrink wrap technology in order to minimize the size of the package.

Some embodiments relate to medicament application devices, such as gloves as described herein, that also include a skirt portion, as described herein. In some embodiments the devices and gloves can include a proximal skirt or shroud portion that protects a larger area of the hand. For example, gloves can include a first distal portion that substantially contacts the digit and a second proximal portion that includes a "skirt" portion having a peripheral diameter at its widest point that wider than the diameter of the first distal portion. In some aspects, the internal diameter of at least a portion of the skirt region is larger than the internal diameter of the widest region of the distal portion of the glove. In some aspects the skirt portion does not aid in maintaining the glove securely to the hand or digit of the user. In other words, in some embodiments the skirt covers a portion of the hand of the user, but is not tight or used to hold the device tightly or securely on the hand/digit. It should be understood that the skirt portion can be useful in providing material that can be grasped for putting or pulling the device onto the digit and hand or removing it (e.g., see FIGS. 3A and 3C. For example, the skirt can be easily grasped in order to put the glove on or in order to remove the glove with undue effort. However, once on, in some embodiments, the skirt does not necessarily have to be configured to secure the device onto the hand or digit. For example, in some aspects, the most proximal part of the skirt must not wrap tightly around the finger or hand such that there is a free edge that can easily be grasped by the thumb and finger(s) of the other hand to pull it off. FIGS. 1-3 depict on example of a device or glove with a "skirt." In some aspects the skirt may extend radially from the first distal portion to a proximal peripheral edge. In some aspects the skirt can cover or protect at least a portion of the hand (e.g., the knuckle or proximal phalanges) at the base of the digit, for example at least a portion of the hand proximal to the metacarpophalangeal joint. FIG. 3 depicts a non-limiting example of this concept. Substantially contacting the digit or a given region of a digit can mean that 50% to about 100% of the digit or region is contacted or any sub value or sub range within that range, for example.

The medicament application devices can include or be made of any suitable material. For example, any material that provides a barrier to or protection to the skin or hand region that will come into contact with the medicament, the region of the body to which the medicament is applied, and/or body fluids. Without being limited thereto, the devices can include or be made of one or more of latex, vinyl (polyvinyl chloride), natural rubber, synthetic rubber (e.g., butyl rubber, nitrile rubber, Viton®, neoprene, and polyisoprene), plastic, paper, cotton, vinyl polyvinyl alcohol, woven cellulosic fibers, and any other like material. The medicament application devices may be elastic or flexible. They can be suitable for a single use or multi-use, and can be disposable, recyclable or reusable.

In some embodiments the kits can include at least two compartments, one that can include the medicament reservoir and another configured to include the medicament application device. The two compartments can be separated or they can be connected. In some aspects, even if separated the two individual compartments can be packaged, sold, or provided as a single product. In some embodiments where the compartments are connected, the at least two compartments can at least partially share at least one wall, border or edge. Non-limiting examples are depicted in FIGS. 4-8. For example, the at least partially shared wall, border or edge may be or include one or more of the dividing edge of a dual compartment foil or plastic pouch (see for example FIG. 6). In some aspects the at least partially shared wall of each of the two separate compartments may be lid or enclosure that can be removed exposing one or both compartments. For example, the wall can be the lid of either the reservoir compartment or the application device compartment, or both.

The kits can include one or more compartments that include or are made of an at least partially rigid material, one or more compartments at least partially including or made of a non-rigid material, or at least one compartment that at least partially includes or is made of a rigid material and at least on compartment that at least partially includes or is made of a non-rigid or flexible material. For example, some embodiments relate to dual compartment kits where both compartments are made of a rigid plastic or polyvinyl chloride. In others, both compartments might be made of a flexible "foil" material. In still others, one compartment might be made of a rigid plastic (e.g., the medicament reservoir) while the other is a non-rigid or flexible plastic, such as a transparent or non-transparent plastic or cellophane film covering the "glove." As used herein "rigid" can mean unable to bend or be forced out of shape, stiff or unyielding, not pliant or flexible, not bendable. Numerically, rigid can mean that a wall of such an article will not under ordinary conditions of usage bend or be depressed by more than 10% or 10 degrees, or any value or sub-range there between. "Flexible" can mean that the article can be easily bent or folded without breaking. Examples, of flexible materials are foils, thin plastic, and cellulose or other polymers, such as Cellophane®. Numerically, flexible can mean something that can be bent more than 10 degrees, for example. In some embodiments of a compartment comprising the medicine or the reservoir, the reservoir and the compartment can be one and the same. For example, a foil pouch can function as both the reservoir and the compartment. As noted above, in some embodiments, the compartments and/or the packaging of the kits or products can be made of a disposable material. In some aspects, the disposable packaging, compartments or wrappers can be made of a material that is suitable for flushing in a toilet or that meets regulatory requirements for something to be flushable or biodegradable, for example.

The kits can include, for example, at least a two compartment container with a lid and sides, where the sides include or are made of a rigid material and the lid includes or is made of either a rigid or a flexible material, which configured to be removed. For example, FIGS. 4-5 depict one non-limiting example of such a kit. The rigid material can include or be made of a plastic, a polymer, a metal, a foil, a paper, or any other like or suitable material. The non-rigid material can include or be made of a plastic, a polymer, a cellulosic material, a rubber, a metal, a foil, a paper, or any other like or otherwise suitable material.

Figure 6:
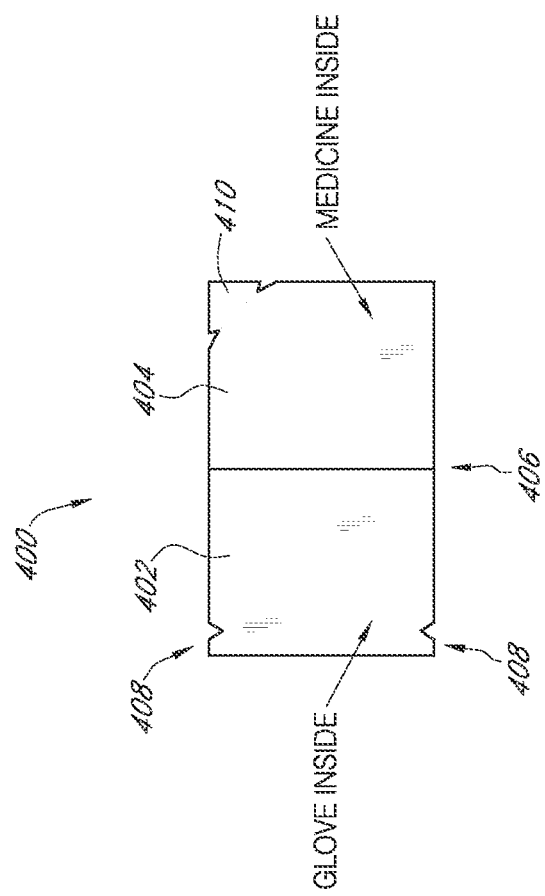
FIG. 6 depicts yet another non-limiting example of one embodiment of dual compartment container, device or system that can be used with the kits and products described herein, and that includes an application device (e.g., a glove or "single-finger" glove) and a medication compartment that can include a specific amount or dosage of the medicine.
Figure 8:
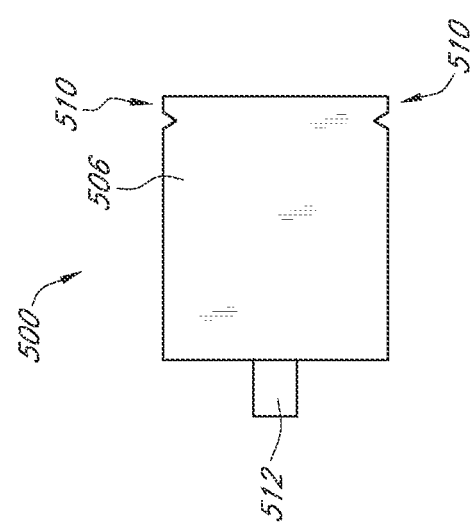
FIG. 8 depicts a side view of the device or system of FIG. 7 that includes an application device (e.g., a glove or "single-finger" glove) and a medication compartment that can include a specific amount or dosage of the medicine.
Figure 7:
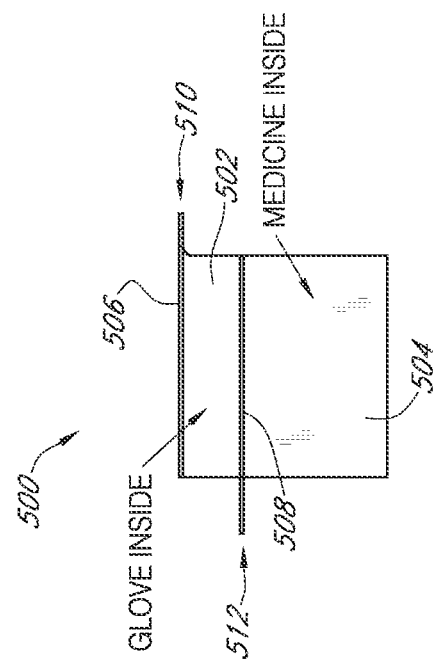
FIG. 7 depicts a top view of a non-limiting example of one embodiment of dual compartment container, device or system that can be used with the kits and products described herein, and that includes an application device (e.g., a glove or "single-finger" glove) and a medication compartment that can include a specific amount or dosage of the medicine.

In some specific embodiments, the kits can include a container that includes or is made from a foil, where the container includes at least two separate compartments at least partially connected on one side or edge, where each compartment is configured to be separately opened. FIG. 6 depicts a non-limiting example of such a container. In some embodiments the kits can include at least one compartment that includes or is made of a rigid material and a separate compartment comprising a non-rigid or flexible material. FIGS. 7-8 depict a non-limiting example of such compartments. It should be understood that in some embodiments, including those depicted in FIGS. 4-8 (which are non-limiting examples), that the devices or gloves can be packaged in a way such that when the compartment or package is properly opened, that the glove or device is presented so that proximal end or skirt end is available for the user to grasp in order to remove the device and then pull it onto the digit (or digits) of the user. As such, in those embodiments, the user can maintain greater sterility (for example) by minimizing or avoiding contact with the distal portion of the glove or device. In such embodiments, the glove or device can be packaged with the compartment or packaging so that it is folded or otherwise in the packaging with an orientation that permits presentation of the proximal end or skirt upon opening.

Some embodiments relate to products that include a plurality of the kits described above and elsewhere herein. The plurality of kits may include, for example, a supply of medicament for a desired period of treatment, such as a period of treatment of 1 day, 2, days, 3 days, 4 days, 5 days, 6 days, 7 days, 8, days, 9 days, 10 days, 2 weeks, 3 weeks, 1 month, and 90 days. Thus, a product can be dispensed to a patient or other user with a sufficient number of single use kits (for example) to last for the desired period of treatment. The products can include sufficient kids for using multiple kits each day; where multiple daily administrations of the medicament are necessary. The products can include a medicament that is administered once daily or multiple times per day.

Still further embodiments relate to methods of applying a medicament and/or treating a condition, which methods can include, for example, providing a kit as described herein; putting the medicament application device onto the appropriate portion of the hand of the user (e.g., onto a finger); removing an amount of the medicament from the reservoir, and contacting at least some of the medicament to a region of the body of a patient that is to be treated. The methods further may include removing the medicament application device from the hand of the user. In embodiments that include a skirt, the skirt can conveniently facilitate removal. For example, the user can grasp at least a portion of the proximal edge of the skirt and pull the device in a direction that is distal to the user. In some preferred aspects this can result in turning the device or glove "inside out" or in other words after removal the inside wall of the device is on the external side of the device. The methods further may include discarding the removed medicament application device.

The methods can be used to treat any of a number of different conditions or promote certain results, including for example, inflammation, allergic reactions, neoplasms, infections, hormone and metabolic disorders, pain, arthritis, impotence or sexual dysfunction, sexually transmitted diseases, anal conditions, vaginal conditions, acne, dry skin, hair loss, hair or skin discoloration, hair growth, skin restoration, wrinkling, sun and age spots, other skin aging and conditions, skin dysfunction (oily skin, unclean skin, etc.), medications to affect muscle tone in a local region, such as perianal phenylephrine for treatment of fecal incontinence, as well as any other like or otherwise suitable condition. Some specific conditions within those categories are listed elsewhere herein. Any suitable medicament or agent can be applied for the various conditions. Several examples of potential sites for application include, without being limited thereto, open wounds, one or both eyes, the mouth, genitalia or the genital area, anal region or anus, ostomies and ostomy incision locations, and the like.

Brief reference and discussion of FIGS. 1-8 will now be made. FIG. 1A depicts a single or one-finger glove 100 with a distal portion 102 that as depicted is a cylinder or tube apparatus, and with a "skirt" 106. The skirt 106 defines an opening 104 through which the single finger can be inserted into the glove 100. The skirt 106 can facilitate the glove 100 being put on and taken off in a convenient and sanitary manner. FIG. 1B depicts a cross-sectional view of the glove 100 across the axis 1B of FIG. 1A. FIG. 1C depicts a bottom view of the glove 100. Referring to FIG. 1C the arrow line designed as 102 illustrates the side walls viewed from a perpendicular vantage, and the arrow line designated with 106 similarly depicts the bottom view of part of the skirt 106. The opening 104 also is shown. The depicted single finger glove 100 can be constructed of any of any suitable material, including for example, latex, vinyl (polyvinyl chloride), rubber, butyl rubber, nitrile rubber, viton, neoprene, polyisoprene, plastic, paper, cotton, vinyl polyvinyl alcohol, and the like or any other suitable material.

Figure 3B:
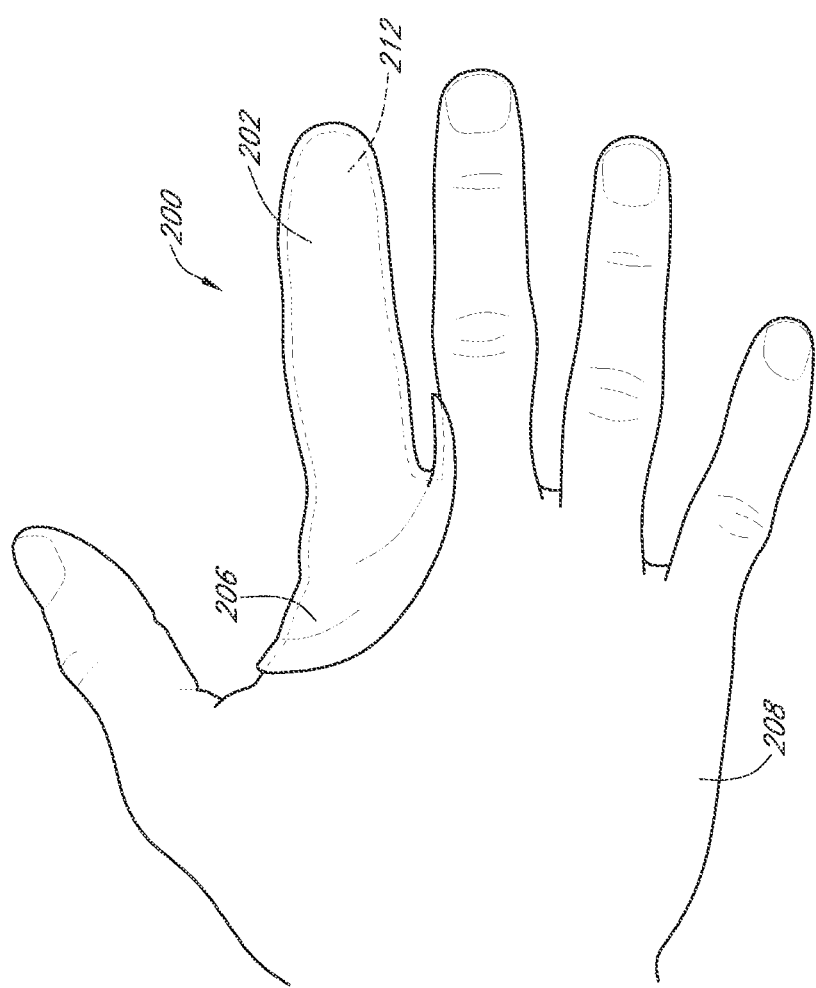
FIG. 3B depicts a non-limiting example of an application device in place on the index finger of a user.
Figure 3C:
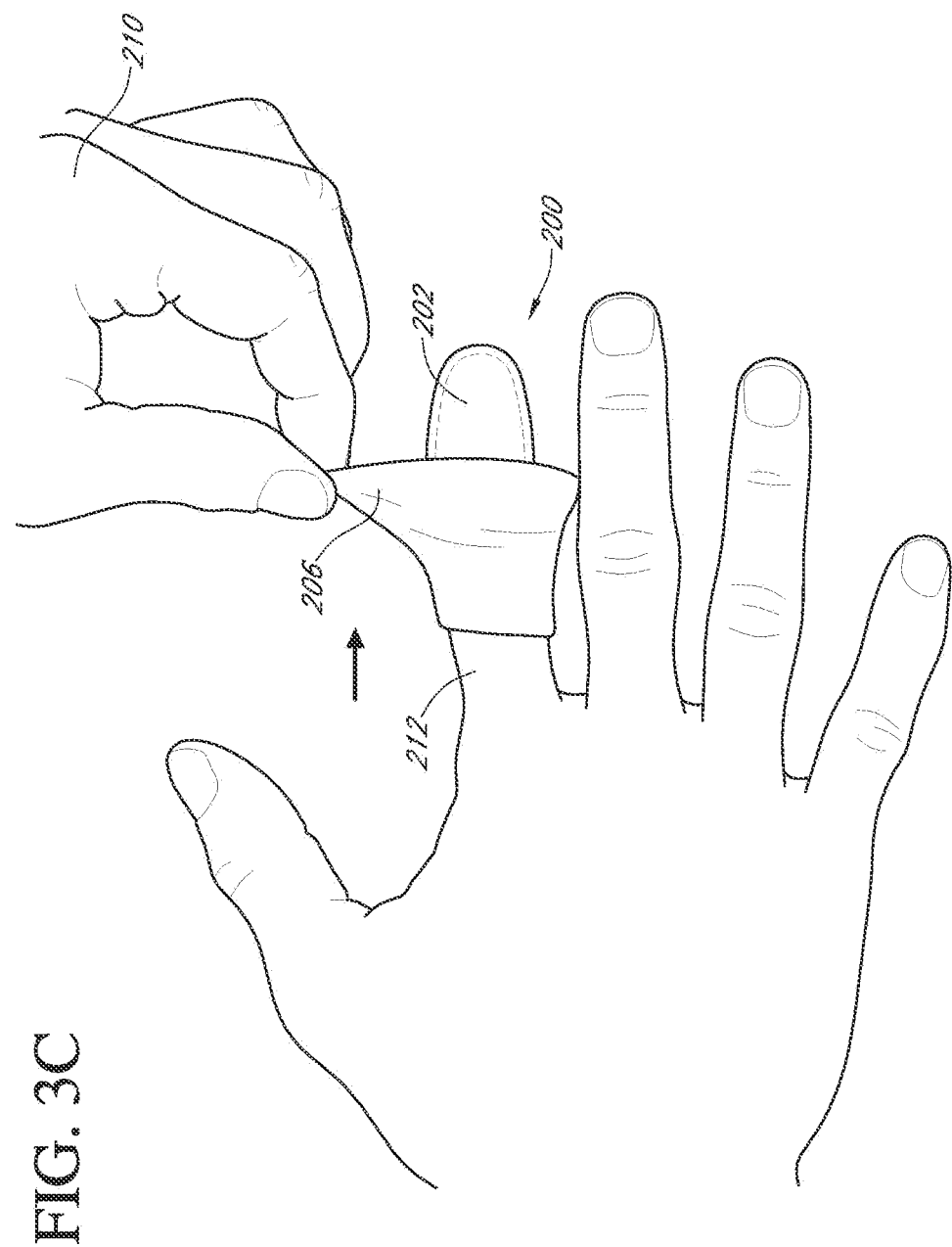
FIG. 3C depicts a non-limiting example of an application device being removed from the index finger of a user. In the depiction, the removed device will be "inside out" such that any material on the application side of the device will be inside the removed device and isolated from contact.

Referring now to FIGS. 3A-3C a single finger glove 200 is depicted on a right human hand 208. Using the hand 210 opposite (left hand in the depiction) to the one that will apply the medication, the user can grasp the skirt 206 of the glove, insert a long finger 212 (e.g., either the index or middle finger) of the other hand 208 (e.g., right hand is depicted) into the distal portion 202 glove; the glove is then secured to the finger by tugging proximally on the skirt. FIG. 3B depicts a single finger glove 200 when in place upon the index finger of the user. The diameter of the distal portion 202 can be of a size that permits the glove to fit onto the finger of the user. Preferably it is of a size that is tight enough to keep the glove securely on the finger when in use, but which also permits the glove to be put on and taken off without too much effort, and preferably without requiring so much force that the device may tear, rip or otherwise be damaged. In some embodiments the gloves can be made out of a material sufficiently flexible that one size would fit almost everyone; a person with an extraordinarily large hand could put the glove on the little finger instead of the index finger, for example.

After properly putting the glove onto the index finger, the user dips the tip of the gloved finger into the medication (e.g., in the rigid or semi-rigid plastic compartment embodiment), or squeezes (e.g., in the flexible, non-rigid or foil embodiment) the medication out of the packet onto the gloved fingertip. The medication is applied by the gloved finger to the desired region (e.g., the anal region). Referring to FIG. 3C, the glove 200 is then removed by tugging distally on the skirt 206 using the ungloved hand 210. The glove 200, now inside out with the soiled portion on the inside, is discarded.

FIGS. 4-8 depict various non-limiting examples of dual compartment containers that can be used in the kits described herein. FIGS. 4-5 depict dual compartment container 300 with a glove compartment 302, a medicament compartment 304 with a medicine reservoir, and removable seals or lid portions 306 and 308. FIG. 4 is a top view of the dual compartment container 300 and FIG. 5 is a side view of the device 300. To further illustrate one example embodiment of the depicted device 300, the following example is provided. A glove and medicine are inside the two compartments 302/304. As depicted the two compartments 302/304 are joined at junction 310. If desired, the junction can be configured to permit the compartments 302/304 to be separated, for example by the junction being perforated or of a releasable adhesive, etc. The two compartments can be made of any suitable material, for example, a rigid or semi-rigid plastic, and can include non-rigid or flexible pull tab tops 306/308, which can be made for example of foil, plastic, paper, etc. The two-compartment package can be disposable. The medicine containing compartment 304 includes a precise unit dose of the topical anal medication. To use the container 300 the user pulls on the tabs to respectively expose the glove and the medication. The tip of the glove finger is dipped into the medication reservoir and the medication is applied as explained elsewhere herein. After use the glove can be removed, for example, as discussed in connection with FIG. 3C.

FIG. 6 depicts a non-limiting example of a dual compartment container 400 with a dual "envelope" or dual "pouch" configuration. The container includes a glove compartment 402 and a medicine compartment 404 that are connected along an edge 406. The glove compartment can be opened by tearing or pulling on either side of the tab 408. The medicine compartment can be opened by tearing or pulling on tab 410. The edge 406 can be a sealed border separating the two compartments, and if desired, can be perforated to permit the two compartments to be separated. In some non-limiting embodiments the container 400 can be a two-compartment foil packet or two one-compartment foil packets that are joined together but easily separated by tearing along a perforated line 406. In use the two tab version depicted as container 400 can be used by pulling on one tab 408 to expose the glove and later pulling on the other tab 410 to expose the medication, which can be removed by squeezing or pinching the compartment to force or expel the medicine through the opening in the corner. The container 400 can be discarded after use along with the used glove.

FIGS. 7-8 depict dual compartment container 500 with a glove compartment 502, a medicament compartment 504 with a medicine reservoir, and removable seals or lid portions 304a and 304b. FIG. 7 is a top view of the dual compartment container 500 and depicts the seal or lid 506 on top of the glove compartment 502 (not visible from the top view due to being covered by the seal/lid 506). The glove compartment seal or lid 506 includes pull tab 510 with notches that can be torn or removed so that the glove can be removed. Also depicted is the pull tab 512 of the medicine compartment 504, which is not visible from the top view. FIG. 8 is a side view of the device 500 and depicts the two compartments 502/504 and the removable seals or lids 506/508, which also include pull tabs 510/512. In some non-limiting embodiments, the containers of FIGS. 7-8 can be constructed, for example, of a single plastic compartment 500 that contains the medication in the lower portion 504 of the single compartment device 500, which is separated from the glove by a foil lid 508 for that compartment 504. The glove lays on top of that lid 508, and there is a second foil lid 506 on top of the glove. A tab 510 with a notch can facilitate tearing open the first foil lid 506 to remove the glove, and a protruding tab 512 would facilitate tearing off the entire second foil lid 508 to expose the medication beneath.

In any of the non-limiting configurations the glove can be packed into a compartment of the plastic container or into a compartment of the foil packet in any suitable manner. In some aspects the glove can be packed in its compartment, for example, by folding it, typically in a "Z" pattern. The skirt of the glove can be configured so as to be presented or be immediately available to the user—either on the top in the case of the plastic container that are opened on top or at the opening in the case of the foil packet or double foil lid.

The foregoing description details certain embodiments of the systems, devices, kits and methods disclosed herein. It will be appreciated, however, that no matter how detailed the foregoing appears in text, the devices, systems, kits and methods can be practiced in many ways. As is also stated above, it should be noted that the use of particular terminology when describing certain features or aspects of the invention should not be taken to imply that the terminology is being re-defined herein to be restricted to including any specific characteristics of the features or aspects of the technology with which that terminology is associated. The scope of the disclosure should therefore be construed in accordance with the appended claims and any equivalents thereof.

It will be appreciated by those skilled in the art that various modifications and changes may be made without departing from the scope of the described technology. Such modifications and changes are intended to fall within the scope of the embodiments, as defined by the appended claims. It will also be appreciated by those of skill in the art that parts included in one embodiment are interchangeable with other embodiments; one or more parts from a depicted embodiment can be included with other depicted embodiments in any combination. For example, any of the various components described herein and/or depicted in the Figures may be combined, interchanged or excluded from other embodiments.

With respect to the use of any plural and/or singular terms herein, those having skill in the art can translate from the plural to the singular and/or from the singular to the plural as is appropriate to the context and/or application. The various singular/plural permutations may be expressly set forth herein for sake of clarity.

It will be understood by those within the art that, in general, terms used herein, and especially in the appended claims (e.g., bodies of the appended claims) are generally intended as "open" terms (e.g., the term "including" should be interpreted as "including but not limited to," the term "having" should be interpreted as "having at least," the term "includes" should be interpreted as "includes but is not limited to," etc.). The term "comprising" as used herein is synonymous with "including," "containing," or "characterized by," and is inclusive or open-ended and does not exclude additional, unrecited elements or method steps.

It will be further understood by those within the art that if a specific number of an introduced claim recitation is intended, such an intent will be explicitly recited in the claim, and in the absence of such recitation no such intent is present. For example, as an aid to understanding, the following appended claims may contain usage of the introductory phrases "at least one" and "one or more" to introduce claim recitations. However, the use of such phrases should not be construed to imply that the introduction of a claim recitation by the indefinite articles "a" or "an" limits any particular claim containing such introduced claim recitation to embodiments containing only one such recitation, even when the same claim includes the introductory phrases "one or more" or "at least one" and indefinite articles such as "a" or "an" (e.g., "a" and/or "an" should typically be interpreted to mean "at least one" or "one or more"); the same holds true for the use of definite articles used to introduce claim recitations. In addition, even if a specific number of an introduced claim recitation is explicitly recited, those skilled in the art will recognize that such recitation should typically be interpreted to mean at least the recited number (e.g., the bare recitation of "two recitations," without other modifiers, typically means at least two recitations, or two or more recitations). Furthermore, in those instances where a convention analogous to "at least one of A, B, and C, etc." is used, in general such a construction is intended in the sense one having skill in the art would understand the convention (e.g., "a system having at least one of A, B, and C" would include but not be limited to systems that have A alone, B alone, C alone, A and B together, A and C together, B and C together, and/or A, B, and C together, etc.). In those instances where a convention analogous to "at least one of A, B, or C, etc." is used, in general such a construction is intended in the sense one having skill in the art would understand the convention (e.g., "a system having at least one of A, B, or C" would include but not be limited to systems that have A alone, B alone, C alone, A and B together, A and C together, B and C together, and/or A, B, and C together, etc.). It will be further understood by those within the art that virtually any disjunctive word and/or phrase presenting two or more alternative terms, whether in the description, claims, or drawings, should be understood to contemplate the possibilities of including one of the terms, either of the terms, or both terms. For example, the phrase "A or B" will be understood to include the possibilities of "A" or "B" or "A and B."

Although the technology has been described with reference to embodiments and examples, it should be understood that numerous and various modifications can be made without departing from the spirit of the invention. Accordingly, the technology is limited only by the following claims. The above description discloses several methods and materials of the present invention. This invention is susceptible to modifications in the methods and materials, as well as alterations in the fabrication methods and equipment. Such modifications will become apparent to those skilled in the art from a consideration of this disclosure or practice of the invention disclosed herein. Consequently, it is not intended that this invention be limited to the specific embodiments disclosed herein, but that it cover all modifications and alternatives coming within the true scope and spirit of the invention.

All references cited herein, including but not limited to published and unpublished applications, patents, and literature references, are incorporated herein by reference in their entirety and are hereby made a part of this specification. To the extent publications and patents or patent applications incorporated by reference contradict the disclosure contained in the specification, the specification is intended to supersede and/or take precedence over any such contradictory material.

The invention claimed is:

1. A product comprising:
    a first compartment having first walls that define a reservoir, the first compartment including a first lid enclosing a medicament within the reservoir; and
    a second compartment having second walls that define a cavity, the second compartment including a second lid enclosing a glove within the cavity;
    wherein the first lid includes a first tab that extends beyond a first periphery of the first compartment and the second lid includes a second tab that extends beyond a second periphery of the second compartment;
    wherein the first compartment and the second compartment are coupled together with the reservoir and the cavity separated and sealed from one another; and
    wherein the first walls of the first compartment and the second walls of the second compartment are semi-rigid or rigid.

2. The product of claim 1, wherein the first tab extends in a first direction and the second tab extends in a second direction different than the first direction.

3. The product of claim 1, wherein the first tab has a first structure or shape and the second tab has a second structure or shape that is different than the first structure or shape.

4. The product of claim 1, wherein (a) the second compartment is positioned on top of the first compartment such that the first lid of the first compartment forms a bottom wall of the second compartment that separates the reservoir and the cavity from one another, or (b) the first compartment is positioned on top of the second compartment such that the second lid of the second compartment forms a bottom wall of the first compartment that separates the reservoir and the cavity from one another.

5. The product of claim 1, wherein the first lid and the second lid are substantially flat and extend over an opening defined at a top of the first walls and the second walls to enclose the reservoir and the cavity, respectively.

6. The product of claim 1, wherein the glove has one finger lumen.

7. The product of claim 1, wherein the glove has two finger lumens.

8. The product of claim 1, wherein the product is configured for a single use prior to disposal.

9. The product of claim 1, wherein the glove is packaged such that, when the second lid is opened, a skirt of the glove is available to be grasped without contacting a distal portion of the glove.

10. The product of claim 9, wherein the skirt extends radially and uniformly outward from a proximal end of the glove.

11. A product comprising:
a first compartment having first walls that define a reservoir, the first compartment including a first lid enclosing a medicament within the reservoir; and
a second compartment having second walls that define a cavity, the second compartment including a second lid enclosing a glove within the cavity;
wherein the first lid includes a first tab that extends beyond a first periphery of the first compartment and the second lid includes a second tab that extends beyond a second periphery of the second compartment;
wherein the first walls and the second walls are joined at a junction that separates the reservoir and the cavity;
wherein the first compartment and the second compartment are coupled together with the reservoir and the cavity separated and sealed from one another; and
wherein the first walls of the first compartment and the second walls of the second compartment are semi-rigid or rigid.

12. A product comprising:
a first compartment having first walls that define a reservoir, the first compartment including a first lid enclosing a medicament within the reservoir; and
a second compartment having second walls that define a cavity, the second compartment including a second lid enclosing a glove within the cavity;
wherein the first lid includes a first tab that extends beyond a first periphery of the first compartment and the second lid includes a second tab that extends beyond a second periphery of the second compartment; and
wherein the first compartment and the second compartment are coupled together with the reservoir and the cavity separated and sealed from one another.

13. The product of claim 12, wherein the first tab extends in a first direction and the second tab extends in a second direction different than the first direction.

14. The product of claim 12, wherein the first tab has a first structure or shape and the second tab has a second structure or shape that is different than the first structure or shape.

15. The product of claim 12, wherein the first walls of the first compartment and the second walls of the second compartment are semi-rigid.

16. The product of claim 12, wherein the first walls of the first compartment and the second walls of the second compartment are rigid.

17. The product of claim 12, wherein the second compartment is positioned on top of the first compartment such that the first lid of the first compartment forms a bottom wall of the second compartment that separates the reservoir and the cavity from one another.

18. The product of claim 12, wherein the first compartment is positioned on top of the second compartment such that the second lid of the second compartment forms a bottom wall of the first compartment that separates the reservoir and the cavity from one another.

19. The product of claim 12, wherein the first walls and the second walls are joined at a junction that separates the reservoir and the cavity.

* * * * *